(12) United States Patent
Roselli

(10) Patent No.: US 10,548,710 B2
(45) Date of Patent: Feb. 4, 2020

(54) METHOD AND APPARATUS FOR TIME-DIFFERENTIAL DEPLOYMENT OF AN ENDOVASCULAR DEVICE WITHIN A BODY LUMEN

(71) Applicant: THE CLEVELAND CLINIC FOUNDATION, Cleveland, OH (US)

(72) Inventor: Eric E. Roselli, Rocky River, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 155 days.

(21) Appl. No.: 15/902,384

(22) Filed: Feb. 22, 2018

(65) Prior Publication Data
US 2018/0243075 A1 Aug. 30, 2018

Related U.S. Application Data

(60) Provisional application No. 62/462,968, filed on Feb. 24, 2017.

(51) Int. Cl.
*A61F 2/07* (2013.01)
*A61F 2/954* (2013.01)
(Continued)

(52) U.S. Cl.
CPC ............. *A61F 2/07* (2013.01); *A61F 2/954* (2013.01); *A61B 2017/00867* (2013.01); *A61F 2002/061* (2013.01); *A61F 2002/9534* (2013.01)

(58) Field of Classification Search
CPC ...... A61F 2/07; A61F 2/954; A61F 2002/061; A61F 2002/077; A61F 2002/9534; A61F 2250/0024; A61F 2250/0065
See application file for complete search history.

(56) References Cited

U.S. PATENT DOCUMENTS 6,613,078 B1 * 9/2003 Barone ............... A61F 2/07
606/194
6,676,694 B1 1/2004 Weiss
(Continued)

FOREIGN PATENT DOCUMENTS

EP 2451409 A2 5/2012
WO 2005/058202 A1 6/2005
(Continued)

OTHER PUBLICATIONS

Chalasani, Naga, Mark A. Deeg, and David W. Crabb. "Systemic levels of lipid peroxidation and its metabolic and dietary correlates in patients with nonalcoholic steatohepatitis." The American journal of gastroenterology 99.8 (2004): 1497.
(Continued)

*Primary Examiner* — Katherine M Rodjom
(74) *Attorney, Agent, or Firm* — Tarolli, Sundheim, Covell & Tummino LLP

(57) ABSTRACT

A tubular first device segment has longitudinally spaced proximal and distal first segment ends. The first device segment includes a first segment lumen. A tubular second device segment has longitudinally spaced proximal and distal second segment ends and a second segment lumen. A tubular eversion structure is located longitudinally intermediate the first and second device segments. The eversion structure has longitudinally spaced proximal and distal eversion ends separated by a tubular eversion structure wall. One of the proximal and distal eversion ends is attached to the first device segment and the other of the proximal and distal eversion ends is attached to the second device segment. At least a portion of the eversion structure wall is configured for selective intussusception into at least one of the first segment lumen, the second segment lumen, and another portion of the eversion structure wall.

22 Claims, 9 Drawing Sheets

(51) Int. Cl.
    *A61F 2/06*         (2013.01)
    *A61F 2/95*         (2013.01)
    *A61B 17/00*       (2006.01)

(56) References Cited

U.S. PATENT DOCUMENTS

| | | |
|---|---|---|
| 7,815,656 B2 | 10/2010 | Rust et al. |
| 8,398,703 B2 | 3/2013 | Kassab et al. |
| 2004/0002714 A1 | 1/2004 | Weiss |
| 2005/0171598 A1 | 8/2005 | Schaeffer |
| 2005/0278013 A1 | 12/2005 | Rust et al. |
| 2005/0288768 A1 | 12/2005 | Sowinski et al. |
| 2006/0173629 A1 | 8/2006 | Poynard |
| 2007/0010874 A1 | 1/2007 | Sun |
| 2007/0037287 A1 | 2/2007 | Takatsuki et al. |
| 2011/0022153 A1* | 1/2011 | Schreck .................. A61F 2/07 623/1.13 |
| 2011/0125244 A1 | 5/2011 | Roeder et al. |
| 2013/0204360 A1* | 8/2013 | Gainor .................. A61F 2/2436 623/2.18 |
| 2014/0336749 A1 | 11/2014 | Bogenschuetz et al. |

FOREIGN PATENT DOCUMENTS

| | | |
|---|---|---|
| WO | 2008/021192 A2 | 2/2008 |
| WO | 2011/005955 A2 | 1/2011 |
| WO | 2016/122862 A1 | 8/2016 |

OTHER PUBLICATIONS

Yoshida, Yasukazu, et al. "Lipid peroxidation in mice fed a choline-deficient diet as evaluated by total hydroxyoctadecadienoic acid." Nutrition 22.3 (2006): 303-311.

Zhang, Renliang, et al. "Defects in leukocyte-mediated initiation of lipid peroxidation in plasma as studied in myeloperoxidase-deficient subjects: systematic identification of multiple endogenous diffusible substrates for myeloperoxidase in plasma." Blood 99.5 (2002): 1802-1810.

PCT International Search Report and Written Opinion for International Application No. PCT/US2018/019155, dated May 7, 2018, pp. 1-11.

* cited by examiner

METHOD AND APPARATUS FOR TIME-DIFFERENTIAL DEPLOYMENT OF AN ENDOVASCULAR DEVICE WITHIN A BODY LUMEN

RELATED APPLICATION

This application claims priority from U.S. Provisional Application No. 62/462,968, filed 24 Feb. 2017, the subject matter of which is incorporated herein by reference in its entirety.

TECHNICAL FIELD

The present invention relates to an apparatus and method for use of an endovascular device and, more particularly, to a method and apparatus for time-differential deployment of an endovascular device within a body lumen.

BACKGROUND OF THE INVENTION

A stent-graft is typically used to provide a prosthetic intraluminal wall. For instance, in the case of a vascular stenosis or aneurysm, the stent-graft may provide an unobstructed conduit for blood in the area of the stenosis or aneurysm. A stent-graft may be endovascularly deployed in a body lumen (e.g., a blood vessel) at the site of a stenosis or aneurysm by so-called "minimally invasive" techniques. These techniques can include compression of the stent-graft radially inward for intraluminal delivery via catheter to the target site, and/or use of a known "cut-down" technique at a location where the target blood vessel is accessible through the patient's skin. When the stent-graft is positioned at the correct location, the stent-graft is caused or allowed to re-expand to a predetermined diameter in the vessel.

Accurately positioning a stent-graft prior to deployment can present challenges, such as impairment of blood flow through a target vessel during deployment. Furthermore, deployment of a stent-graft within a thoracic aorta (ascending aorta) may implicate added maneuverability and placement challenges of higher blood flow rate and pressure as compared to lower flow and pressure conditions within an abdominal aorta (descending aorta). For these and other reasons, a user may desire a stent-graft which reduces disruption of fluid flow during deployment.

SUMMARY OF THE INVENTION

In an embodiment of the present invention, an endovascular stent-graft is described. A tubular first device segment has longitudinally spaced proximal and distal first segment ends. The first device segment includes a first stent structure with an attached first graft structure substantially restricting lateral fluid flow therethrough. The first device segment has an inner first segment surface defining a first segment lumen and an outer first segment surface configured for selective contact with a vessel wall installation site. A tubular second device segment has longitudinally spaced proximal and distal second segment ends. The second device segment includes a second stent structure with an attached second graft structure substantially restricting lateral fluid flow therethrough. The second device segment has an inner second segment surface defining a second segment lumen and an outer second segment surface configured for selective contact with the vessel wall installation site. A tubular eversion structure is located longitudinally intermediate the first and second device segments. The eversion structure has longitudinally spaced proximal and distal eversion ends separated by a tubular eversion structure wall. At least a portion of the eversion structure substantially permits lateral fluid flow therethrough. One of the proximal and distal eversion ends is attached to the first device segment and the other of the proximal and distal eversion ends is attached to the second device segment. At least a portion of the eversion structure wall is configured for selective intussusception into at least one of the first segment lumen, the second segment lumen, and an other portion of the eversion structure wall. Such intussusception substantially restricts lateral fluid flow through the eversion structure.

In an embodiment of the present invention, a method of time-differential deployment of an endovascular device within a body lumen is described. An endovascular device having proximal and distal device ends longitudinally separated by a tubular device body is provided. The device body at least partially permits fluid flow through a thickness thereof. The device body includes at least two circumferential hinge joints. A first device segment is defined longitudinally between the distal device end and a first hinge joint. A second device segment is defined longitudinally between a second hinge joint and the proximal device end. An intermediate device segment is defined longitudinally between the first and second device segments. The endovascular device is collapsed. The collapsed endovascular device is surrounded with a constraining sheath. The first device segment is deployed within the body lumen at a first time by withdrawing the constraining sheath proximally from the first device segment while maintaining an absolute longitudinal position of the endovascular device within the body lumen. The intermediate device segment within the body lumen is partially deployed by withdrawing the constraining sheath proximally from the intermediate device segment while maintaining an absolute longitudinal position of the endovascular device within the body lumen. The constraining sheath and second device segment are moved distally while an absolute longitudinal position of the deployed first device segment within the body lumen is maintained. The intermediate device segment is inverted within the body lumen by rotating the intermediate device segment about the first hinge joint with respect to the first device segment and by rotating the intermediate device segment about the second hinge joint with respect to the second device segment. The second device segment is deployed within the body lumen at a second time by withdrawing the constraining sheath proximally from the second device segment while maintaining an absolute longitudinal position of the deployed first device segment within the body lumen. Fluid flow is permitted through a thickness of the partially deployed intermediate device segment during an interim time period between the first and second times.

In an embodiment of the present invention, a method of sequentially deploying an endovascular device is described. An endovascular device is provided. The endovascular device includes a tubular first device segment with longitudinally spaced first proximal and distal ends which has an inner first segment surface defining a first segment lumen and an outer first segment surface configured for selective contact with a vessel wall installation site. The first device segment is configured to substantially restrict lateral fluid flow therethrough. A tubular second device segment with longitudinally spaced second proximal and distal ends has an inner second segment surface defining a second segment lumen and an outer second segment surface configured for selective contact with the vessel wall installation site. The second device segment is configured to substantially restrict lateral fluid flow therethrough. A tubular eversion structure is located longitudinally intermediate the first and second device segments. The eversion structure has longitudinally spaced proximal and distal eversion ends separated by a tubular eversion structure wall having an inner eversion structure surface and an outer eversion structure surface. The proximal eversion end is attached to the first device segment and the distal eversion end is attached to the second device segment. The endovascular device is laterally collapsed. The collapsed endovascular device is surrounded with a longitudinally extending sheath. The sheath, with the enclosed endovascular device, is inserted into a vessel. The sheath, with the enclosed endovascular device, is placed laterally adjacent a vessel wall installation site. The sheath is retracted proximally from the first device segment of the endovascular device. The first device segment is expanded at the vessel wall installation site at a first time. The vessel wall installation site is laterally contacted with the outer first segment surface. The sheath is retracted proximally from at least a portion of the eversion structure. The vessel wall installation site is laterally contacted with the eversion distal end while the eversion proximal end is maintained in a collapsed condition within the sheath. Lateral fluid flow is permitted through at least a portion of the eversion structure. The sheath is moved distally within the vessel while the collapsed second device segment is maintained within the sheath. At least a portion of the eversion structure is inverted to bring the proximal eversion end at least one of laterally adjacent to and distally beyond the distal eversion end. The sheath is retracted proximally from the second device segment of the endovascular device. The second device segment is expanded at the vessel wall installation site at a second time, temporally spaced from the first time. The vessel wall installation site is laterally contacted with the outer second segment surface. At least a portion of the inner eversion structure surface is laterally contacted with at least one of the inner first segment surface, the inner second segment surface, and an other portion of the inner eversion structure surface. At least a portion of the outer eversion structure surface is laterally contacted with at least one of the outer first segment surface, the outer second segment surface, and an other portion of the outer eversion structure surface. Longitudinal fluid flow through the vessel is maintained by directing the fluid flow laterally through at least a portion of the eversion structure during an interim time period between the first and second times.

BRIEF DESCRIPTION OF THE DRAWINGS

For a better understanding of the invention, reference may be made to the accompanying drawings, in which.

DESCRIPTION OF ASPECTS OF THE DISCLOSURE

Figure 1:
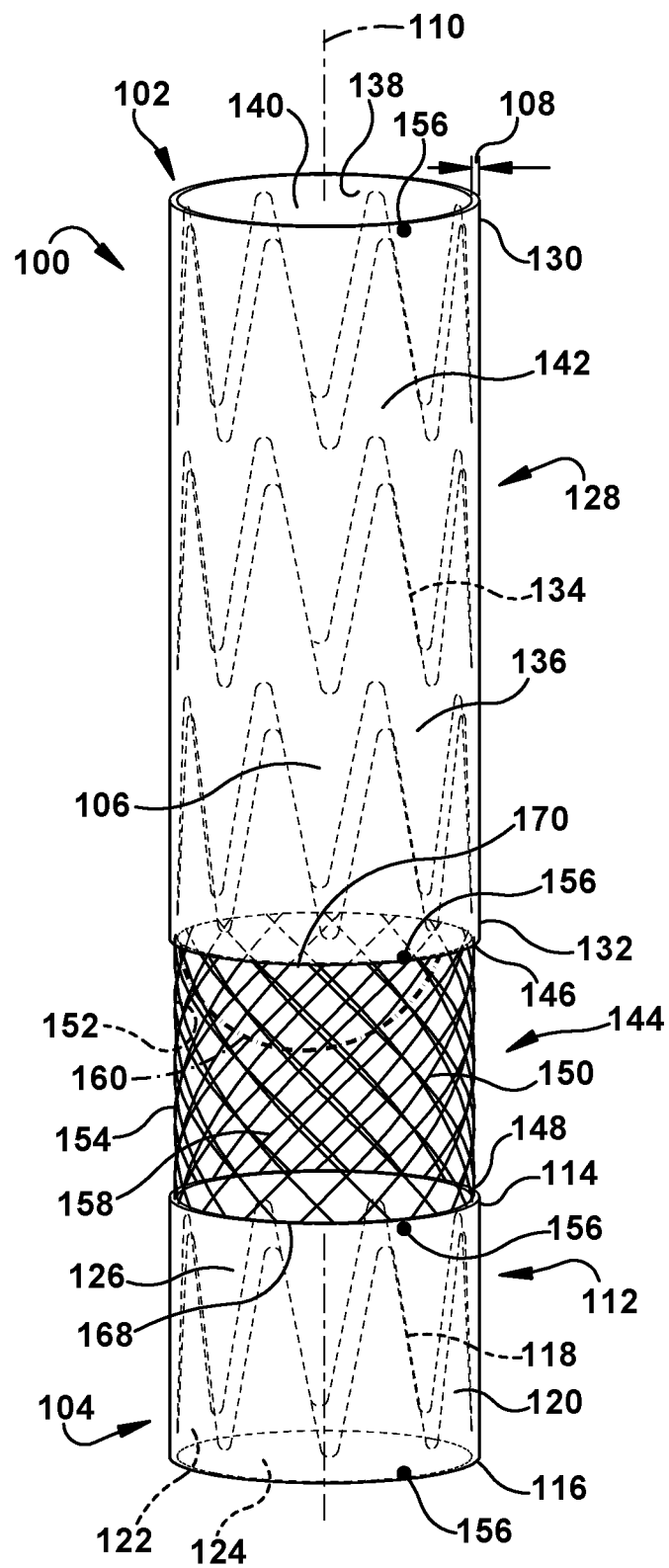
FIG. 1 is a schematic side view of one embodiment of the present invention.

Unless defined otherwise, all technical and scientific terms used herein have the same meaning as is commonly understood by one of skill in the art to which the present disclosure pertains.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, farm animals, livestock, etc.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

In accordance with the present invention, FIG. 1 depicts an endovascular device 100, also known as a "stent-graft", having proximal and distal device ends 102 and 104, respectively, longitudinally separated by a tubular device body 106. The device body 106 at least partially permits fluid flow through a thickness thereof. The term "thickness" is used herein to indicate a "wall" portion of the device body 106, as viewed in a direction oriented laterally to a longitudinal axis 110 in FIG. 1. One of ordinary skill in the art will understand that the relationship of the "thickness" of the device body 106 to the longitudinal axis 110 will change in different configurations of the endovascular device 100, and that the thickness of all parts of the device body will not always be oriented laterally to a longitudinal axis defined by the endovascular device in general, as will become apparent shortly. An example portion of the thickness of the device body 106 is indicated at 108 in FIG. 1.

A tubular first device segment 112 of the endovascular device 100 has longitudinally spaced proximal and distal first segment ends 114 and 116, respectively. The first device segment 112 includes a first stent structure 118 with an attached first graft structure 120 substantially restricting lateral fluid flow therethrough. The term "stent" is used herein to reference a short narrow metal or plastic tube, often in the form of a mesh, that is inserted into the lumen of an anatomical vessel; a "stent" here is a framework-type construct. The term "graft" is used herein to reference a natural or artificial tissue which, when present, may at least partially cover (and be supported by) the stent. As with the previously discussed thickness 108, the "lateral" direction through a particular structure will not always refer to a direction transverse to the longitudinal axis 110 but may instead shift with respect to the longitudinal axis as the subject structure shifts.

The first device segment 112 has an inner first segment surface 122 defining a first segment lumen 124, and an outer first segment surface 126 configured for selective contact with a vessel wall installation site.

A tubular second device segment 128 of the endovascular device 100 has longitudinally spaced proximal and distal second segment ends 130 and 132, respectively. The second device segment 128 includes a second stent structure 134 with an attached second graft structure 136 substantially restricting lateral fluid flow therethrough. The second device segment 128 has an inner second segment surface 138 defining a second segment lumen 140, and an outer second segment surface 142 configured for selective contact with the vessel wall installation site.

A tubular eversion structure 144 is located longitudinally intermediate the first and second device segments 112 and 128. The eversion structure 144 has longitudinally spaced proximal and distal eversion ends 146 and 148, respectively, separated by a tubular eversion structure wall 150. At least a portion of the eversion structure 144 substantially permits lateral fluid flow therethrough. For example, at least a portion of the eversion structure 144 could be made of an open-celled mesh, as shown in FIG. 1. One of the proximal and distal eversion ends 146 and 148 is attached to the first device segment 112 and the other of the proximal and distal eversion ends is attached to the second device segment 128. In the configuration of FIG. 1, the proximal eversion end 146 is attached to the second device segment 128 and the distal eversion end 148 is attached to the first device segment 112. More specifically, in the embodiment shown, the proximal eversion end 146 is attached directly to the distal second segment end 132 and the distal eversion end 148 is attached directly to the proximal first segment end 114.

At least a portion of the eversion structure wall 150 is configured for selective intussusception, as will be described below, into a flow-preventing arrangement with an other portion of the endovascular device, such as at least one of the first segment lumen 124, the second segment lumen 140, and an other portion of the eversion structure wall. The term "intussusception" here is used to indicate a drawing in of something from without, such as an invagination and/or nesting into an overlapping arrangement. The described intussusception substantially restricts lateral fluid flow through the portion of the eversion structure wall 150 by effectively blocking the "flowthrough" areas of the eversion structure wall with a solid or otherwise flow-preventing structure. Contact between the eversion structure wall 150 and the flow-preventing structure, regardless of the nature thereof, is optional so long as lateral fluid flow through the portion of the eversion structure wall is substantially prevented.

The eversion structure 144 may include an inner eversion structure surface 152 and an outer eversion structure surface 154. During intussusception, the inner eversion structure surface 152 may directly laterally contact at least a portion of at least one of the inner first segment surface 122. The outer eversion structure surface 154 may directly laterally contact at least a portion of at least one of the outer first segment surface 126 and the outer second segment surface 142. This direct lateral contact, when present, helps to perform the flow-preventing function previously described.

The endovascular device 100 may include at least one radiopaque marker 156 (four shown). The radiopaque marker(s) 156, when present, may assist the user with locating and/or orienting the endovascular device 100 within a patient's anatomy using radiography or other locating techniques.

The eversion structure 144 may include an eversion stent structure 158 (shown in FIG. 1 as the aforementioned mesh construct) with an attached eversion graft structure 160 (optional, and shown in dash-dot line) partially restricting lateral fluid flow therethrough. It is contemplated that the eversion graft structure 160, when present, may fully cover the eversion stent structure 158 but include a plurality of apertures (not shown) to allow the permeability and fluid flowthrough described below.

Figure 2A:
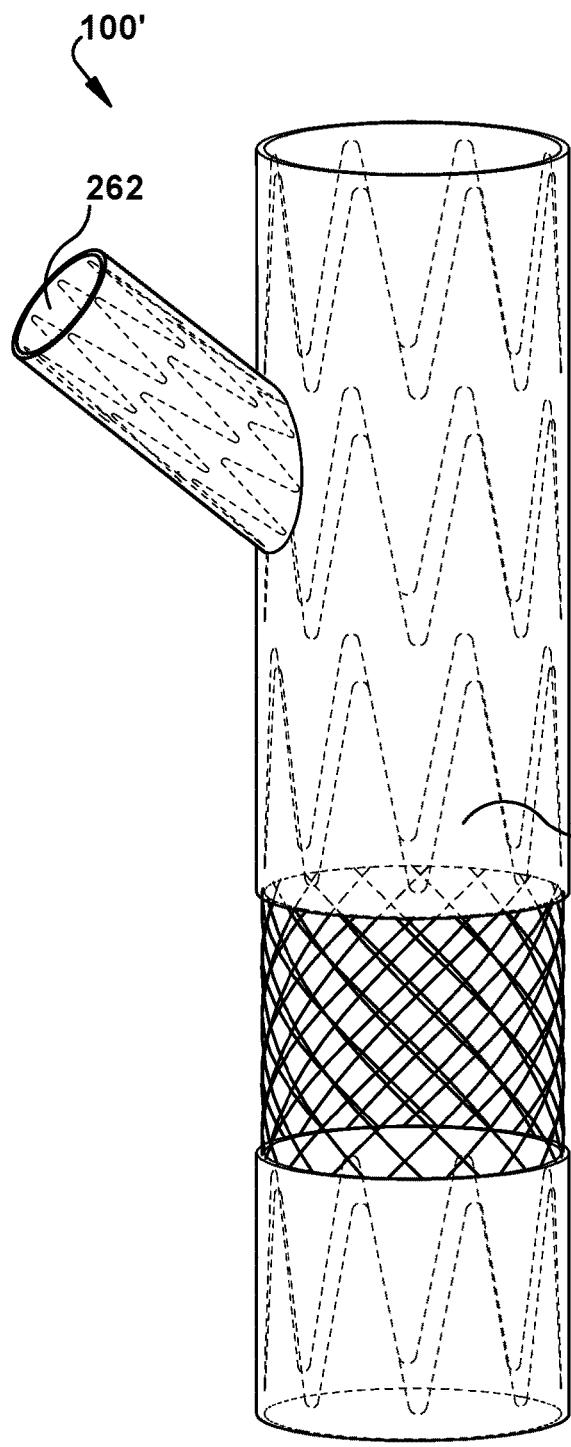
FIG. 2A-2C are schematic side views illustrating optional alternate features of the embodiment of FIG. 1.
Figure 2B:
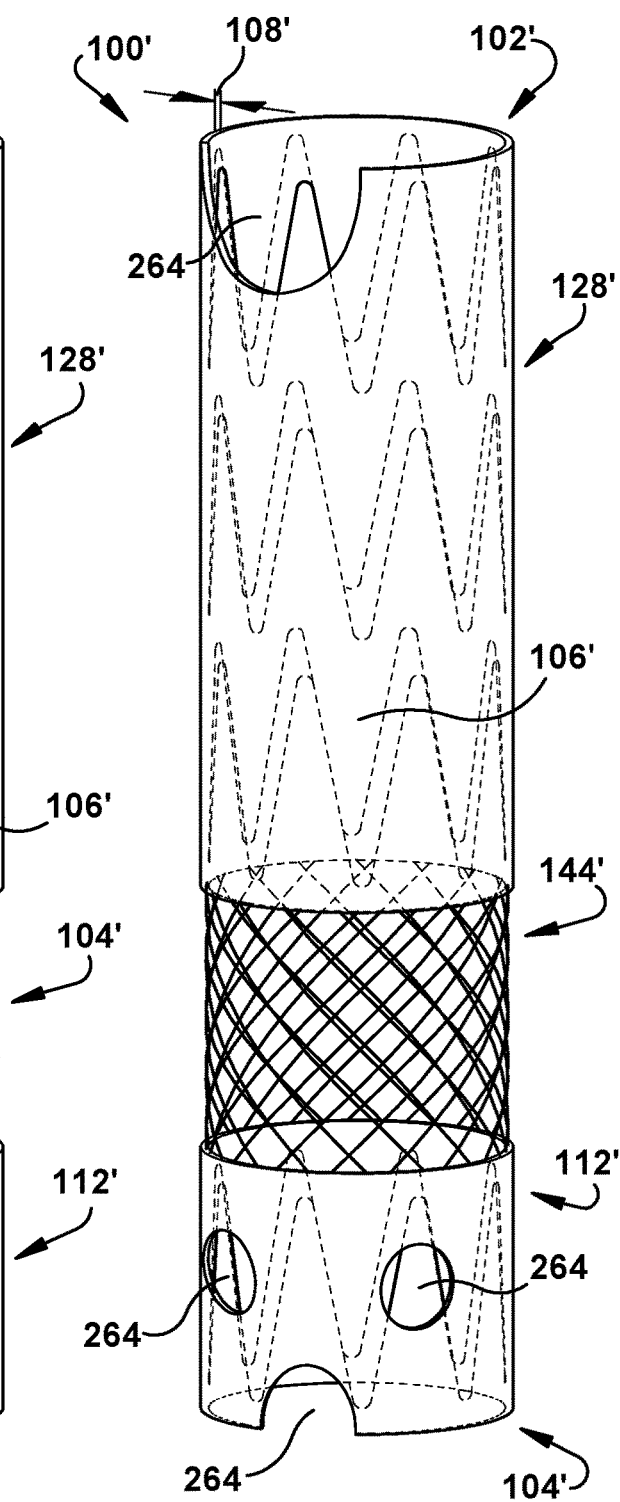
Figure 2C:
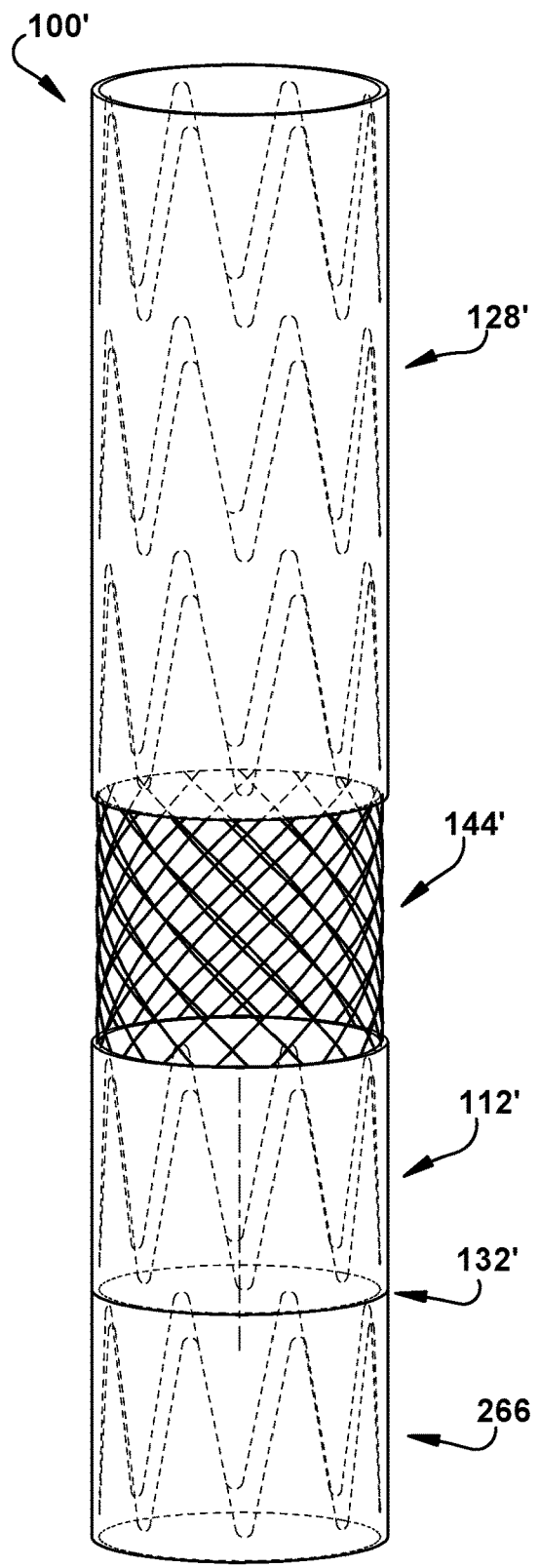

FIGS. 2A-2C depict optional alternate features available for the endovascular device 100', singly or in combination. The endovascular devices 100' of FIGS. 2A-2C are similar to the endovascular device 100 of FIG. 1 and therefore, structures of FIG. 2A-2C that are the same as or similar to those described with reference to FIG. 1 have the same reference numbers with the addition of a "prime" mark.

In FIG. 2A, at least one secondary lumen 262 is provided. The secondary lumen(s) 262, when present, may extend laterally (as shown in FIG. 2, out of the thickness of the endovascular device 100', regardless of the angle formed by the secondary lumen with the device body 106') from at least one of the first device segment 112', the second portion 128', and the eversion structure 144'. The secondary lumen(s) 262 may extend from one or more of the eversion structure 144' and the first and second device segments 112' and 128'. The secondary lumen 262 may be defined by an extension or branch of another structure of the endovascular device 100' (e.g., by a branch of the second device segment 128 as shown here) and/or by a separate stent and/or graft structure (not shown).

FIG. 2B depicts an endovascular device 100' having at least one aperture 264 formed in the device body 106'. The aperture(s) 264, when present, may be located in any suitable position and orientation on the endovascular device 100' and may intersect one or more of the proximal and distal device ends 102' and 104'. The aperture 264 may substantially allow lateral fluid flow through the thickness 108' of the device body 106', or another structure (for example, a mesh filter [not shown]) may be located within or across the aperture to at least partially block fluid flow through the thickness of the device body. An aperture 264 may be associated with a secondary lumen (omitted from FIG. 2B). The endovascular device 100' may be designed such that an aperture 264 is formed in a graft section at a location with no included beams or strands of the associated stent section, or such that an aperture 264 in a graft section exposes at least a portion of the stent section. One of ordinary skill in the art can readily design an endovascular device 100' having one or more apertures 264 with any suitable, location, orientation, shape, size, or other physical characteristics.

The endovascular device 100' of FIG. 2C includes an eversion structure 144' and first and second device segments 112' and 128', as well as an additional device segment, shown here as third device segment 266. The third device segment 266 is shown as having a similar structure to those of the first and second device segments 112' and 128' and as being located adjacent, and connected to, the distal second segment end 132'. However, the third device segment 266 may have any suitable structure and be located in any desired position relative to other structures of the endovascular device 100'. Any number of additional device segments may be provided to an endovascular device 100', whether for adding length and/or flexibility to the endovascular device or for any other purpose.

With reference again to FIG. 1, the connection between the eversion structure 144 and the first and second device segments 112 and 128 may be configured to create at least two circumferential hinge joints, with first and second hinge joints 168 and 170 shown in FIG. 1. The first device segment 112 may be defined longitudinally between the distal device end 104 and the first hinge joint 168. The second device segment 128 may be defined longitudinally between the second hinge joint 170 and the proximal device end 102. An intermediate device segment, referenced herein as an eversion structure 144, may be defined longitudinally between the first and second device segments 112 and 128.

It should be noted here that the described attachments, structures, and connections comprising the endovascular device 100 are not limited to those specifically shown and described. It is contemplated that the endovascular device 100 may be integrally formed or made up of component parts, and that additional structures may be located intermediate those depicted in the Figures.

Additionally, structures specifically indicated need not be separately delineated from other described structures, but could merely be a portion of those other described structures that performs the specifically indicated function. For example, using an example of the first and second hinge joints 168 and 170, the composition of the eversion structure 144 itself at/near the proximal and distal eversion ends 146 and 148 may provide the hereafter described hinging functions. In such case, no separate hinge joints will be required. One of ordinary skill in the art will recognize that a sufficiently flexible eversion structure 144, first device segment 112, and/or second device segment 128 could bend in a hinging manner at any desired point along the length thereof, and such bending could be managed to provide the hinging functions without a separate hinge structure. In the described embodiment, however, it is presumed that each of the eversion structure 144, first device segment 112, and second device segment 128 is semi-rigid (i.e., resistant to bending) in the longitudinal direction and that the rotation-permitting function of the first and second hinge joints 168 and 170 is provided by the means interposed between the eversion structure 144 and the first and second device segments 112 and 128. This means may be sutures or rings (not shown) or any other suitable structure serving to attach the components together, or may be a grooved area, reduced-thickness area, pre-folded seam, or any other suitable structure serving to delineate a hinge joint for an endovascular device 100 which is at least partially integrally formed.

Regardless of the design or nature of the first and second hinge joints 168 and 170, however, the hinging ability of the endovascular device 100 helps to facilitate sequential, time-differential deployment of the endovascular device within a body lumen, as shown in the sequence of FIGS. 3-8.

Figure 3:
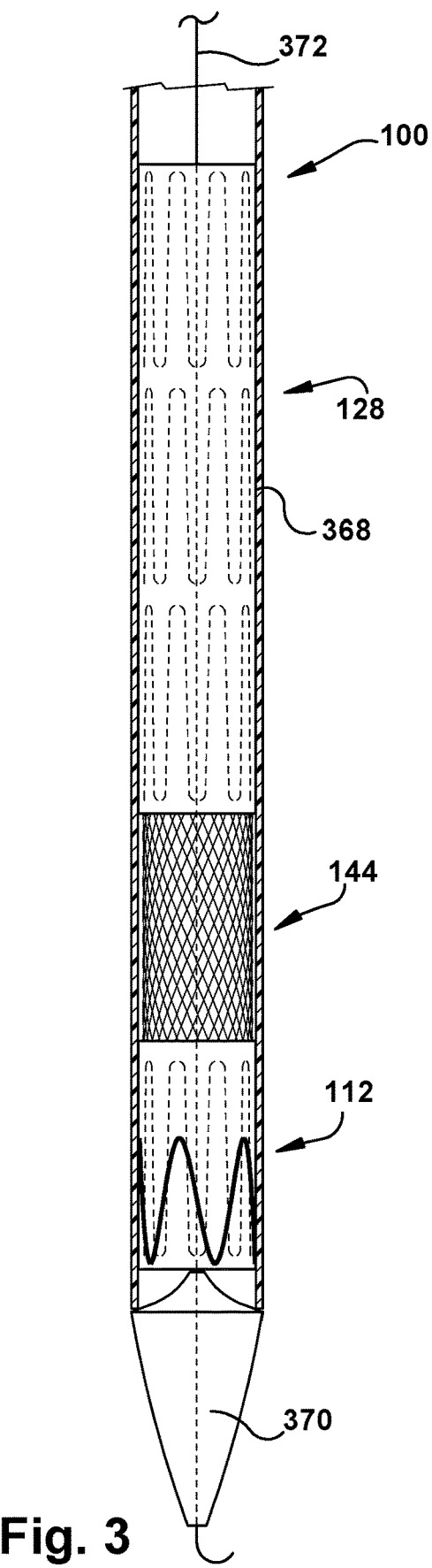
FIG. 3 is a schematic side view of the embodiment of FIG. 1 in a use configuration.

FIG. 3 depicts the endovascular device 100 in a laterally collapsed configuration, for insertion into a patient. In FIG. 3, the endovascular device 100 has been surrounded with a longitudinally extending constraining sheath 372. For ease of description, it is presumed herein that the endovascular device 100 is self-expanding. For example, the first and/or second stent structures 118 and 134, or any other portions of the endovascular device 100, may be made from a shape memory material, such as, but not limited to, NiTinol™. One of ordinary skill in the art will realize that the endovascular device 100 could instead be expanded using a balloon or other suitable means, and will readily be able to design a deployment system for an endovascular device 100 corresponding to a particular application of the present invention.

Figure 4:
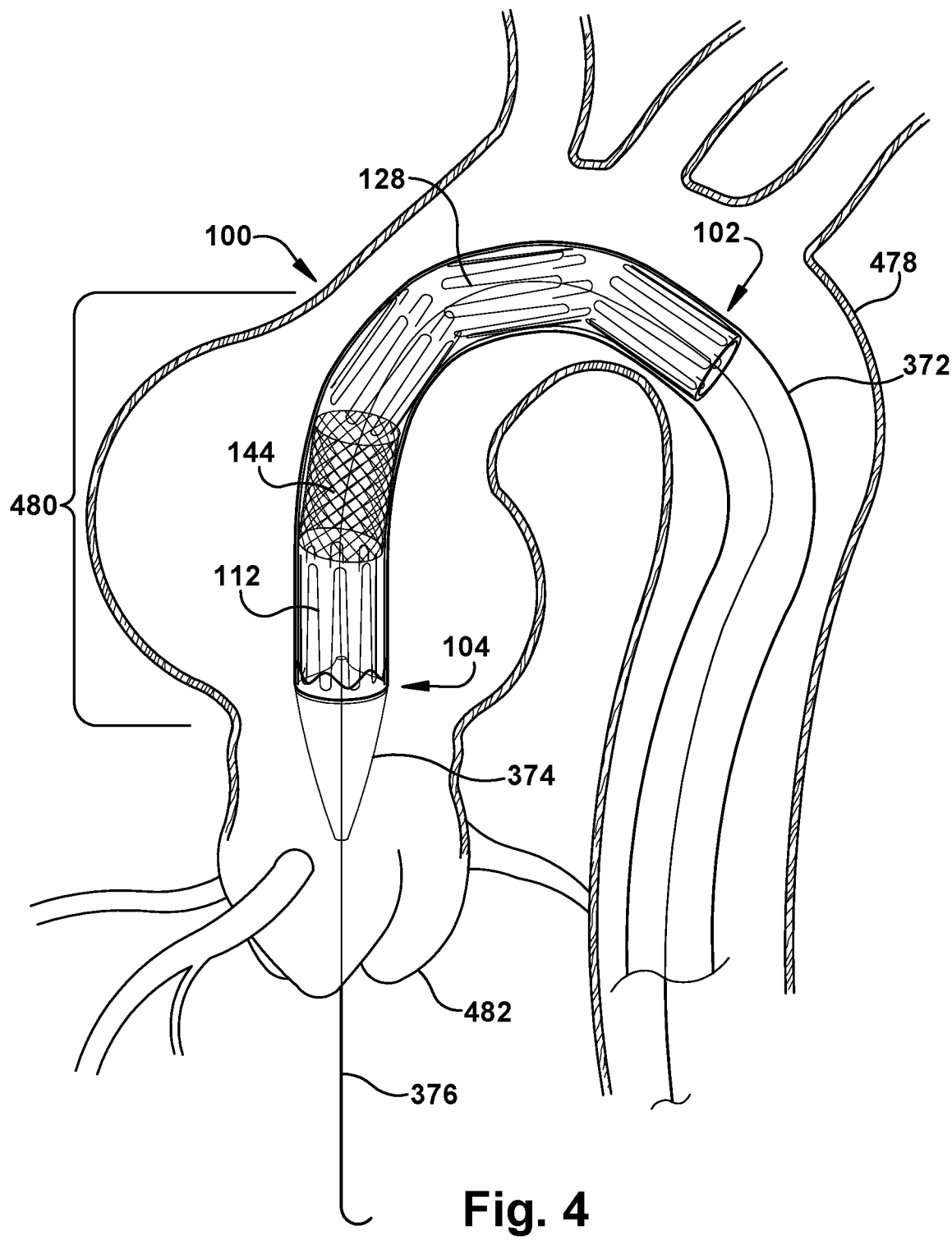
FIGS. 4-8 are schematic side views depicting a sequence of installation of the embodiment of FIG. 1.

In FIG. 3, a nose cone 374 and guidewire 376 are provided in a known manner, to facilitate insertion and deployment of the endovascular device 100. Any other suitable features or structures may be provided to assist a user with inserting the constraining sheath 372, with the enclosed endovascular device 100, into a patient's body lumen in the position shown in FIG. 4. FIG. 4 depicts the body lumen as a blood vessel 478 and, more specifically, a descending aorta, but the technology of the endovascular device 100 could be used in any location at which the user wishes to provide time-differential deployment of a device. In FIG. 4, the guidewire 376 has been passed through an aortic valve 480 to guide the advancing constraining sheath 372 through the patient's vasculature to a position laterally adjacent a vessel wall installation site, indicated generally at 480.

Figure 5:
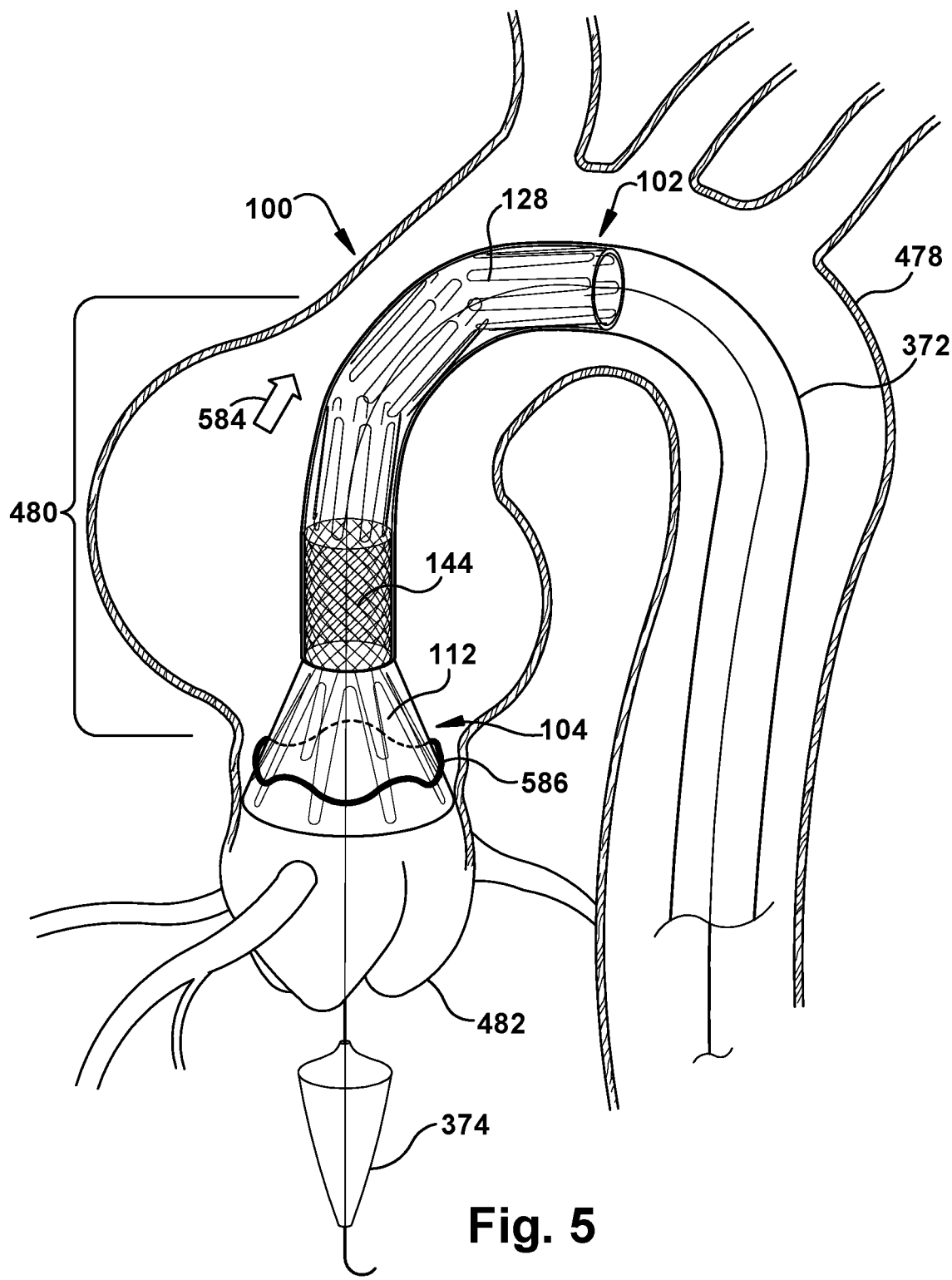
Figure 6:
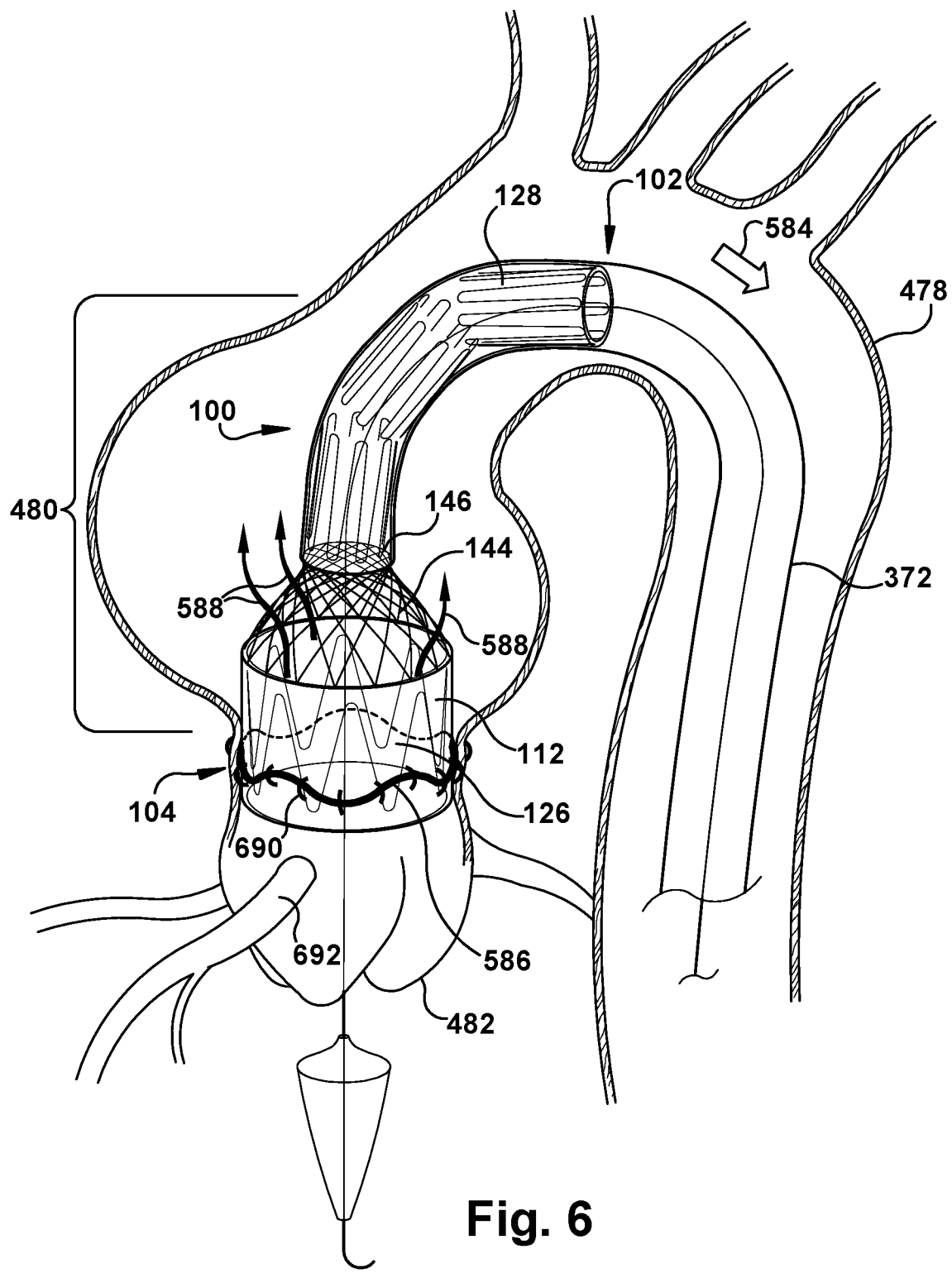

FIG. 5 depicts the endovascular device 100 in an early stage of deployment. At a first time during the deployment sequence, a portion of which is shown schematically in FIG. 5, the constraining sheath 372 is retracted or withdrawn in the proximal direction (indicated by arrow 584) to release and deploy the first device segment 112 within the vessel 478. Because, as previously established, the endovascular device 100 discussed herein includes self-expanding features, withdrawal of the constraining sheath 372 will allow the first device segment 112 to self-expand at the vessel wall installation site 480, as shown in the sequence of FIGS. 5-6. During withdrawal of the constraining sheath 372 at the first time (which will likely occur over a relatively brief expanse of time rather than an instantaneous event), the absolute longitudinal position of the endovascular device 100 as a whole is maintained within the vessel 478.

One or more anchoring aids may be provided to the endovascular device 100, and may be connected to at least one of the first device segment 112, the second device segment 128, and/or the eversion structure 144. For example, a sewing cuff 586, which may include radiopaque features, may be provided at or near the distal device end 104, as shown in FIG. 5.

In FIG. 6, the first device segment 112 has been expanded to bring the outer first segment surface 126 into lateral contact with the vessel wall installation site 480, while the second device segment 128 is still maintained within the constraining sheath 372. The constraining sheath 372 has been retracted in the proximal direction 584 from at least a portion of the eversion structure 144 to at least partially deploy the eversion structure within the vessel 478. During this withdrawal or retraction of the constraining sheath 372, the absolute longitudinal position of the endovascular device 100 as a whole is maintained within the vessel 478.

When the endovascular device 100 is in the configuration of FIG. 6, fluid flow through the vessel 478 is substantially maintained because at least a portion of the eversion structure 144 permits lateral (that is, through the thickness of the eversion structure) fluid flow therethrough, as shown by flow arrows 588 in FIG. 6. The endovascular device 100 accordingly allows the user to perform tasks at the vessel wall installation site 480 or elsewhere in the vessel 478 or the patient's body with a minimum of interruption to the natural fluid flow. For example, the user could apply one or more sutures 690, staples, clips, or any other suitable means to attach the sewing cuff 588, and/or another anchoring aid, to the vessel wall installation site 480 during the interim time period that fluid is flowing laterally through the eversion structure 144 or a portion thereof. As another example, the first device segment 112 could maintain patency of the vessel 478 while the aortic valve 480 is resected. When a secondary lumen 262 is provided, the interim time period could provide an opportunity for deployment. The secondary lumen 262, for instance, could be extended between at least one of the first device segment 112, the second device segment 128, and the eversion structure 144 and a branch vessel, such as the coronary vessel 692 shown in FIG. 6. (The branch vessel need not be located in longitudinal coincidence with the endovascular device 100 at the vessel wall installation site 480, but could be located proximal or distal to the final position of the installed endovascular device.) Regardless of the task(s), if any, carried out during the interim time period, it is anticipated, though not necessary, that this interim time period will be longer than a mere momentary pause in the deployment sequence of the endovascular device 100.

Prior art systems for endovascular deployment require that bloodflow through the vessel 478 be interrupted or diverted during the entire deployment procedure, and the user therefore must work "against the clock" to perform any interim tasks, such as suturing a device to a vessel wall, which must be performed before bloodflow can resume. Conversely, when the endovascular device 100 is used in a vascular application, the patient's natural bloodflow may be interrupted for a shorter time period than currently available due to the permeability of the eversion structure 144 to the bloodflow through the vessel 478.

Figure 7:
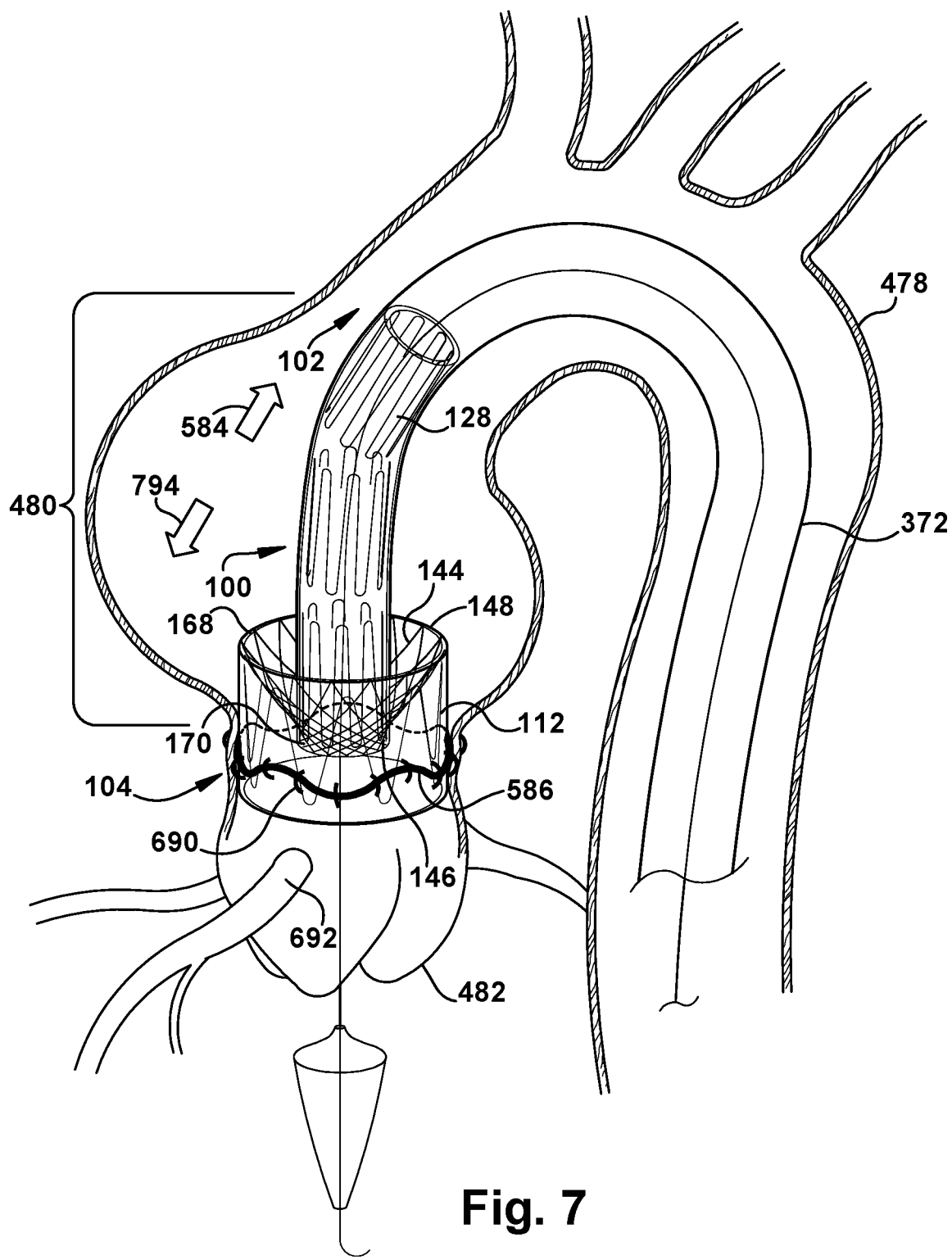

FIG. 7 depicts the endovascular device 100 during a later stage of deployment, at a second time, which is temporally spaced from the first time. As with FIG. 5 and the first time, the sequence depicted in FIGS. 7-8 as occurring at the second time will likely occur over a relatively brief expanse of time rather than being an instantaneous event. It is contemplated, however, that the endovascular device 100 will be in the configuration of FIG. 6 for an interim time period, lasting as long as desired by the user, which temporally separates the first time and the second time.

In the configuration of FIG. 7, the constraining sheath 372, with the collapsed second device segment 128 maintained inside, has been moved distally (in the direction of arrow 794) within the vessel 478, while the absolute longitudinal position of the deployed first device segment 112 has not changed. This advancement of the second device segment 128 in the distal direction 794 causes at least a portion of the eversion structure 144 to invert within the vessel 478 by bringing the proximal eversion end 146 at least one of laterally adjacent to and distally beyond the distal eversion end 148. This inversion of the eversion structure 144 may be accomplished by rotating the eversion structure 144 about the first hinge joint 168 with respect to the first device segment 112 and by rotating the eversion structure about the second hinge joint 170 with respect to the second device segment 128. Optionally, the constraining sheath 372 may have been moved slightly proximally with respect to the eversion structure 144 between the configurations of FIGS. 6 and 7 in order to release the proximal eversion end 146, when the proximal eversion end is held within the constraining sheath 372 as shown during the interim time period.

In FIG. 7, the eversion structure 144 is depicted as being intussuscepted into the first device segment 112. However, it is contemplated that the eversion structure 144 may be rotated about the first hinge joint 168 and about the second hinge joint 170 in the opposite direction to that shown to intussuscept the eversion structure 144 into the second device segment 128, instead.

Regardless of the direction in which the eversion structure 144 is inverted, the second device segment 128 may be deployed within the vessel 478 at the second time by retracting or withdrawing the constraining sheath 372 proximally from the second device segment while maintaining the absolute longitudinal position of the first device segment 112 within the vessel. Therefore, the second device segment 128 is released and allowed to expand such that at least a portion of the outer second segment surface 142 is allowed to come into lateral contact with the vessel wall installation site 480. Optionally, and as shown in FIG. 8, there may be some longitudinal overlap between the first and second device segments 112 and 128 so that at least a portion of the inner first segment surface 122 comes into lateral contact with at least a portion of the outer second segment surface 128.

More broadly, however, when the endovascular device 100 is in the fully deployed configuration, at least a portion of the inner eversion structure surface 152 may come into at least partial lateral contact with at least one of the inner first segment surface 122, the inner second segment surface 138, and an other portion of the inner eversion structure surface. Similarly, at least a portion of the outer eversion structure surface 154 may come into at least partial lateral contact with at least one of the outer first segment surface 126, the outer second segment surface 142, and an other portion of the outer eversion structure surface. One of ordinary skill in the art can readily provide an endovascular device 100 wherein any desired structures come into any degree of, or even no, contact with other structures of the endovascular device, for a particular application of the present invention.

Figure 8:
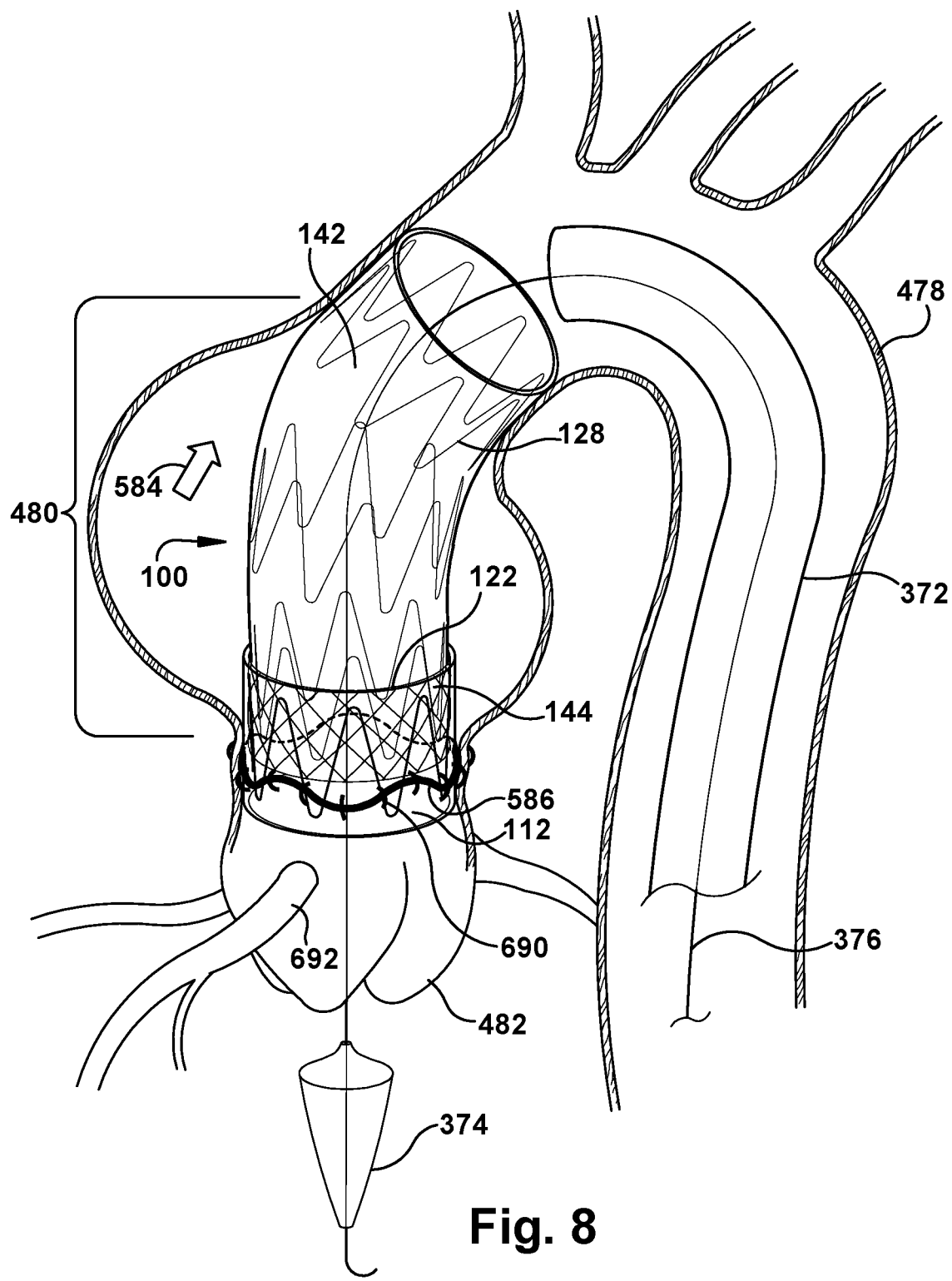

Once the endovascular device 100 has reached the fully deployed configuration shown in FIG. 8, the constraining sheath 372, guidewire 376, and nose cone 374 may be removed from the patient's body and the surgical procedure concluded as desired.

Figure 9:
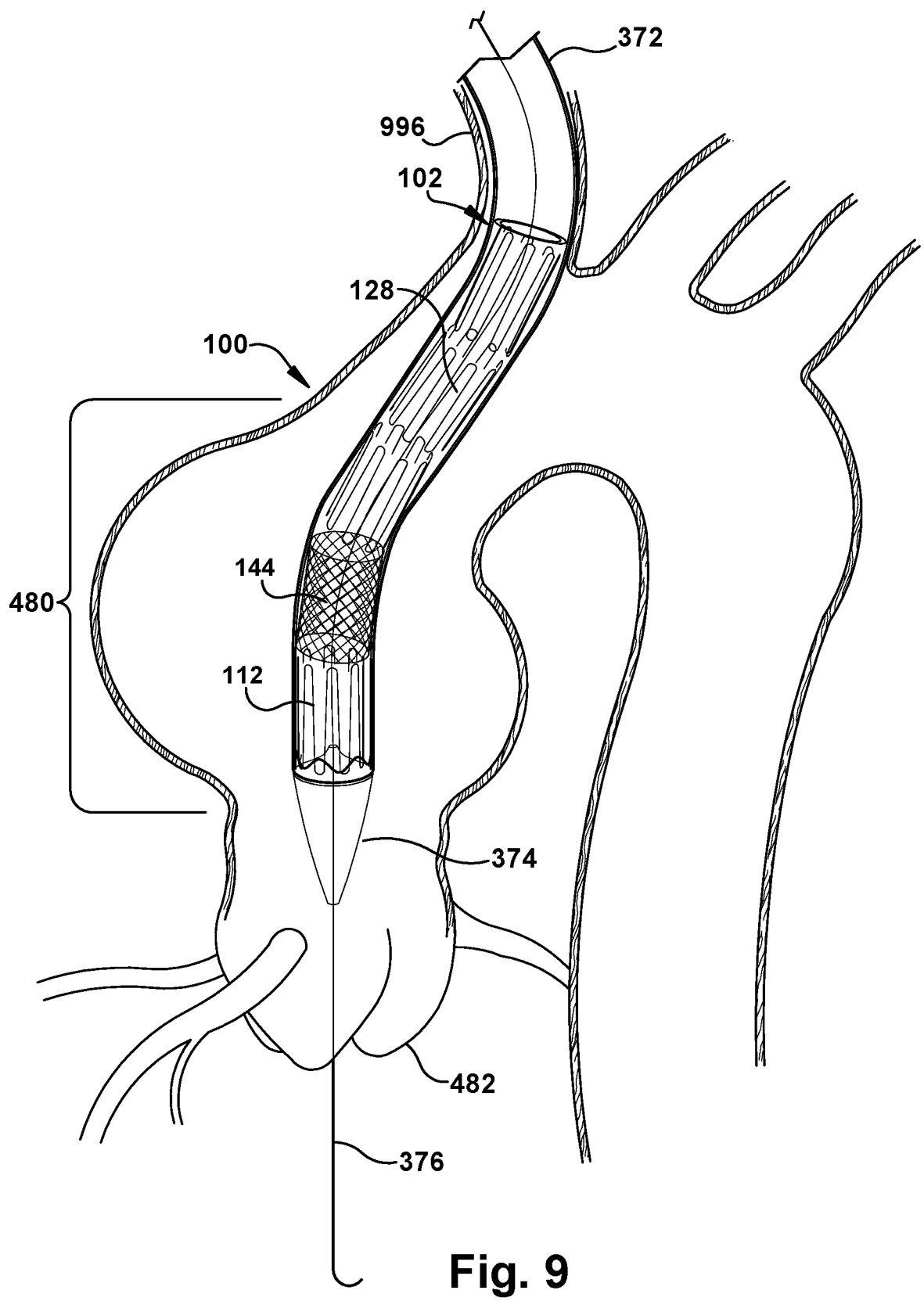
FIG. 9 is a schematic side view depicting an alternate installation option of the embodiment of FIG. 1.

In the sequence of FIGS. 4-8, the endovascular device 100 is shown as entering the aortic arch from the descending aorta. However, when the patient's vasculature is used for access to the vessel wall installation site 480, any desired technique and route may be used for passage of the endovascular device 100 into and through the vasculature. For example, in the alternate installation option depicted in FIG. 9, the vessel is a brachiocephalic artery 996. While the present Figures therefore depict two example paths for placement of the endovascular device 100 in a target vessel wall installation site 480, one of ordinary skill in the art will understand how to route and position an endovascular device 100 in any desired installation location, using any suitable congenital, acquired, or purpose-provided lumen for passage of the endovascular device through the patient's body as needed.

While aspects of the present invention have been particularly shown and described with reference to the preferred embodiment above, it will be understood by those of ordinary skill in the art that various additional embodiments may be contemplated without departing from the spirit and scope of the present invention. For example, the structures comprising the endovascular device 100 may be made of any suitable material or combination of materials, though it is contemplated that the materials used for implantation will be biocompatible, and may have any suitable configuration and arrangement. One or more of the first and second device segments 112 and 128, the eversion structure 144, and/or the secondary lumen 262 may be longitudinally tapered or otherwise contoured for a desired interaction with other structures of the endovascular device 100 or the vessel 478. The eversion structure 144 could function as a filtering member to trap debris or other particulate matter carried by the fluid flowing laterally through the eversion structure during the interim time period; if so, the debris could be removed by the user or trapped within the structure of a fully deployed endovascular device 100. The described process could be reversed for removal of the endovascular device 100 from the patient's body, either during the same surgical procedure as the deployment or at a later time. One or more prosthetic valves (not shown) could be carried by and/or within one or more of the first and second device segments 112 and 128, the eversion structure 144, and/or the secondary lumen 262. A graft structure may be located inside and/or outside an associated stent structure, and may be attached thereto in any suitable manner. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, I claim:

1. An endovascular stent-graft, comprising:
    a tubular first device segment having longitudinally spaced proximal and distal first segment ends, the first device segment including a first stent structure with an attached first graft structure substantially restricting lateral fluid flow therethrough, and the first device segment having an inner first segment surface defining a first segment lumen and an outer first segment surface configured for selective contact with a vessel wall installation site;
    a tubular second device segment having longitudinally spaced proximal and distal second segment ends, the second device segment including a second stent structure with an attached second graft structure substantially restricting lateral fluid flow therethrough, and the second device segment having an inner second segment surface defining a second segment lumen and an outer second segment surface configured for selective contact with the vessel wall installation site; and
    a tubular eversion structure located longitudinally intermediate the first and second device segments, the eversion structure having longitudinally spaced proximal and distal eversion ends separated by a tubular eversion structure wall, at least a portion of the eversion structure substantially permitting lateral fluid flow therethrough, one of the proximal and distal eversion ends being attached to the first device segment and the other of the proximal and distal eversion ends being attached to the second device segment; wherein at least a portion of the eversion structure wall is configured for selective intussusception into at least one of the first segment lumen, the second segment lumen, and another portion of the eversion structure wall, such intussusception substantially restricting lateral fluid flow through the eversion structure.

2. The endovascular stent-graft of claim 1, wherein the first and second device segments are each selectively collapsible for endovascular insertion through a blood vessel and positioning at the vessel wall installation site, the first and second device segments are each selectively expandable for deployment at the vessel wall installation site, the expansion of the first device segment is temporally spaced from the expansion of the second device segment, and fluid flows laterally through the eversion structure during an interim time period between the expansion of the first device segment and the expansion of the second device segment.

3. The endovascular stent-graft of claim 1, including an anchoring aid directly attached to at least one of the first and second device segments and configured for attachment to the vessel wall installation site during the interim time period.

4. The endovascular stent-graft of claim 3, wherein the anchoring aid is a first anchoring aid, and a second anchoring aid is directly attached to at least one of the first and second device segments and configured for attachment to the vessel wall installation site during the interim time period.

5. The endovascular stent-graft of claim 1, including at least one radiopaque marker.

6. The endovascular stent-graft of claim 1, including at least one secondary lumen extending laterally from at least one of the first device segment, the second device segment, and the eversion structure.

7. The endovascular stent-graft of claim 6, wherein the secondary lumen is configured to extend between at least one of the first device segment, the second device segment, and the eversion structure and a branch vessel projecting into the vessel wall.

8. The endovascular stent-graft of claim 1, wherein the eversion structure includes an inner eversion structure surface and an outer eversion structure surface, and, during intussusception, the inner eversion structure surface directly laterally contacts at least a portion of at least one of the inner first segment surface and the inner second segment surface and the outer eversion structure surface directly laterally contacts at least a portion of at least one of the outer first segment surface and the outer second segment surface.

9. The endovascular stent-graft of claim 1, wherein the eversion structure includes an eversion stent structure with an attached eversion graft structure partially restricting lateral fluid flow therethrough.

10. The endovascular stent-graft of claim 1, wherein the proximal eversion end is attached directly to the distal second segment end and the distal eversion end is attached directly to the proximal first segment end.

11. A method of time-differential deployment of an endovascular device within a body lumen, the method comprising the steps of:
    providing an endovascular device having proximal and distal device ends longitudinally separated by a tubular device body, the device body at least partially permitting fluid flow through a thickness thereof, and the device body including at least two circumferential hinge joints;
    defining a first device segment longitudinally between the distal device end and a first hinge joint;
    defining a second device segment longitudinally between a second hinge joint and the proximal device end;

defining an intermediate device segment longitudinally between the first and second device segments;
collapsing the endovascular device;
surrounding the collapsed endovascular device with a constraining sheath;
deploying the first device segment within the body lumen at a first time by withdrawing the constraining sheath proximally from the first device segment while maintaining an absolute longitudinal position of the endovascular device within the body lumen;
partially deploying the intermediate device segment within the body lumen by withdrawing the constraining sheath proximally from the intermediate device segment while maintaining an absolute longitudinal position of the endovascular device within the body lumen;
moving the constraining sheath and second device segment distally while maintaining an absolute longitudinal position of the deployed first device segment within the body lumen;
inverting the intermediate device segment within the body lumen by rotating the intermediate device segment about the first hinge joint with respect to the first device segment and by rotating the intermediate device segment about the second hinge joint with respect to the second device segment;
deploying the second device segment within the body lumen at a second time by withdrawing the constraining sheath proximally from the second device segment while maintaining an absolute longitudinal position of the deployed first device segment within the body lumen; and
permitting fluid flow through a thickness of the partially deployed intermediate device segment during an interim time period between the first and second times.

12. The method of claim 11, wherein at least a portion of the device body includes a tubular, longitudinally-extending stent.

13. The method of claim 11, wherein at least a portion of the device body includes a tubular, longitudinally-extending graft.

14. The method of claim 11, including the steps of:
substantially restricting fluid flow through a thickness of at least one of the first and second device segments; and
substantially permitting fluid flow through a thickness of the intermediate device segment.

15. The method of claim 11, wherein the step of deploying the second device segment within the body lumen at a second time includes the step of laterally contacting at least a portion of an inner surface of the first device segment with at least a portion of an outer surface of the second device segment.

16. The method of claim 11, further including the steps of:
providing an anchoring aid connected to at least one of the first portion, the second portion, and the eversion structure; and
attaching the anchoring aid to the vessel wall installation site during the interim time period.

17. The method of claim 16, wherein the anchoring aid is a first anchoring aid, and including the steps of:
providing a second anchoring aid connected to at least one of the first portion, the second portion, and the eversion structure; and
attaching the second anchoring aid to the vessel wall installation site during the interim time period.

18. The method of claim 11, including the steps of:
providing the endovascular device with at least one secondary lumen extending laterally from at least one of the first portion, the second portion, and the eversion structure; and
extending the secondary lumen between at least one of the first portion, the second portion, and the eversion structure and a branch vessel projecting into the vessel wall.

19. A method of sequentially deploying an endovascular device, the method comprising the steps of:
providing an endovascular device having:
a tubular first device segment with longitudinally spaced first proximal and distal ends, the first device segment having an inner first segment surface defining a first segment lumen and an outer first segment surface configured for selective contact with a vessel wall installation site, the first device segment being configured to substantially restrict lateral fluid flow therethrough,
a tubular second device segment with longitudinally spaced second proximal and distal ends, the second segment having an inner second segment surface defining a second segment lumen and an outer second segment surface configured for selective contact with the vessel wall installation site, the second device segment being configured to substantially restrict lateral fluid flow therethrough, and
a tubular eversion structure located longitudinally intermediate the first and second device segments, the eversion structure having longitudinally spaced proximal and distal eversion ends separated by a tubular eversion structure wall having an inner eversion structure surface and an outer eversion structure surface, the proximal eversion end being attached to the first device segment and the distal eversion end being attached to the second device segment;
laterally collapsing the endovascular device;
surrounding the collapsed endovascular device with a longitudinally extending sheath;
inserting the sheath, with the enclosed endovascular device, into a vessel;
placing the sheath, with the enclosed endovascular device, laterally adjacent a vessel wall installation site;
retracting the sheath proximally from the first device segment of the endovascular device;
expanding the first device segment at the vessel wall installation site at a first time;
laterally contacting the vessel wall installation site with the outer first segment surface;
retracting the sheath proximally from at least a portion of the eversion structure;
laterally contacting the vessel wall installation site with the eversion distal end while maintaining the eversion proximal end in a collapsed condition within the sheath;
permitting lateral fluid flow through at least a portion of the eversion structure;
moving the sheath distally within the vessel while maintaining the collapsed second device segment within the sheath;
inverting at least a portion of the eversion structure to bring the proximal eversion end at least one of laterally adjacent to and distally beyond the distal eversion end;
retracting the sheath proximally from the second device segment of the endovascular device;

expanding the second device segment at the vessel wall installation site at a second time, temporally spaced from the first time;

laterally contacting the vessel wall installation site with the outer second segment surface;

laterally contacting at least a portion of the inner eversion structure surface with at least one of the inner first segment surface, the inner second segment surface, and another portion of the inner eversion structure surface;

laterally contacting at least a portion of the outer eversion structure surface with at least one of the outer first segment surface, the outer second segment surface, and another portion of the outer eversion structure surface; and maintaining longitudinal fluid flow through the vessel by directing the fluid flow laterally through at least a portion of the eversion structure during an interim time period between the first and second times.

20. The method of claim 19, further including the steps of:

providing an anchoring aid connected to at least one of the first device segment, the second device segment, and the eversion structure; and attaching the anchoring aid to the vessel wall installation site during the interim time period.

21. The method of claim 20, wherein the anchoring aid is a first anchoring aid, and including the steps of:

providing a second anchoring aid connected to at least one of the first device segment, the second device segment, and the eversion structure; and attaching the second anchoring aid to the vessel wall installation site during the interim time period.

22. The method of claim 19, including the steps of:

providing the endovascular device with at least one secondary lumen extending laterally from at least one of the first device segment, the second device segment, and the eversion structure; and extending the secondary lumen between at least one of the first device segment, the second device segment, and the eversion structure and a branch vessel projecting into the vessel wall.

* * * * *